United States Patent
Dobashi et al.

(10) Patent No.: US 7,923,680 B2
(45) Date of Patent: Apr. 12, 2011

(54) ANALYSIS METHOD AND ANALYSIS APPARATUS

(75) Inventors: Kazuya Dobashi, Nirasaki (JP); Shigeru Kawamura, Nirasaki (JP); Kohei Tsugita, Nirasaki (JP); Teruyuki Hayashi, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 239 days.

(21) Appl. No.: 12/280,845

(22) PCT Filed: Jun. 21, 2007

(86) PCT No.: PCT/JP2007/062526
§ 371 (c)(1), (2), (4) Date: Aug. 27, 2008

(87) PCT Pub. No.: WO2008/010385
PCT Pub. Date: Jan. 24, 2008

(65) Prior Publication Data
US 2009/0218483 A1    Sep. 3, 2009

(30) Foreign Application Priority Data
Jul. 19, 2006    (JP) .................................. 2006-196946

(51) Int. Cl.
*H01J 49/00* (2006.01)

(52) U.S. Cl. ....................................... 250/281; 250/282
(58) Field of Classification Search .................. 250/281, 250/282, 492.1, 492.2
See application file for complete search history.

(56) References Cited

U.S. PATENT DOCUMENTS

| | | |
|---|---|---|
| 5,426,057 A | 6/1995 | Tamaoki |
| 5,633,172 A | 5/1997 | Shimazaki |
| 6,037,270 A * | 3/2000 | Kageyama et al. ............ 438/746 |
| 2003/0073240 A1 | 4/2003 | Mizuno |

FOREIGN PATENT DOCUMENTS

| | | |
|---|---|---|
| JP | 4 164251 | 6/1992 |
| JP | 6 283582 | 10/1994 |
| JP | 7 161791 | 6/1995 |
| JP | 8 237709 | 9/1996 |
| JP | 2001 208743 | 8/2001 |
| JP | 2006 32859 | 2/2006 |

* cited by examiner

*Primary Examiner* — Kiet T Nguyen
(74) *Attorney, Agent, or Firm* — Oblon, Spivak, McClelland, Maier & Neustadt, L.L.P.

(57) ABSTRACT

An analysis apparatus includes a first process part for removing a film formed on a substrate by irradiating the film with ultraviolet light, a second process part for providing a solution onto a surface of the substrate for dissolving an object being analyzed on the substrate, and a third process part for analyzing the object being analyzed in the solution that is used in the second step.

12 Claims, 9 Drawing Sheets

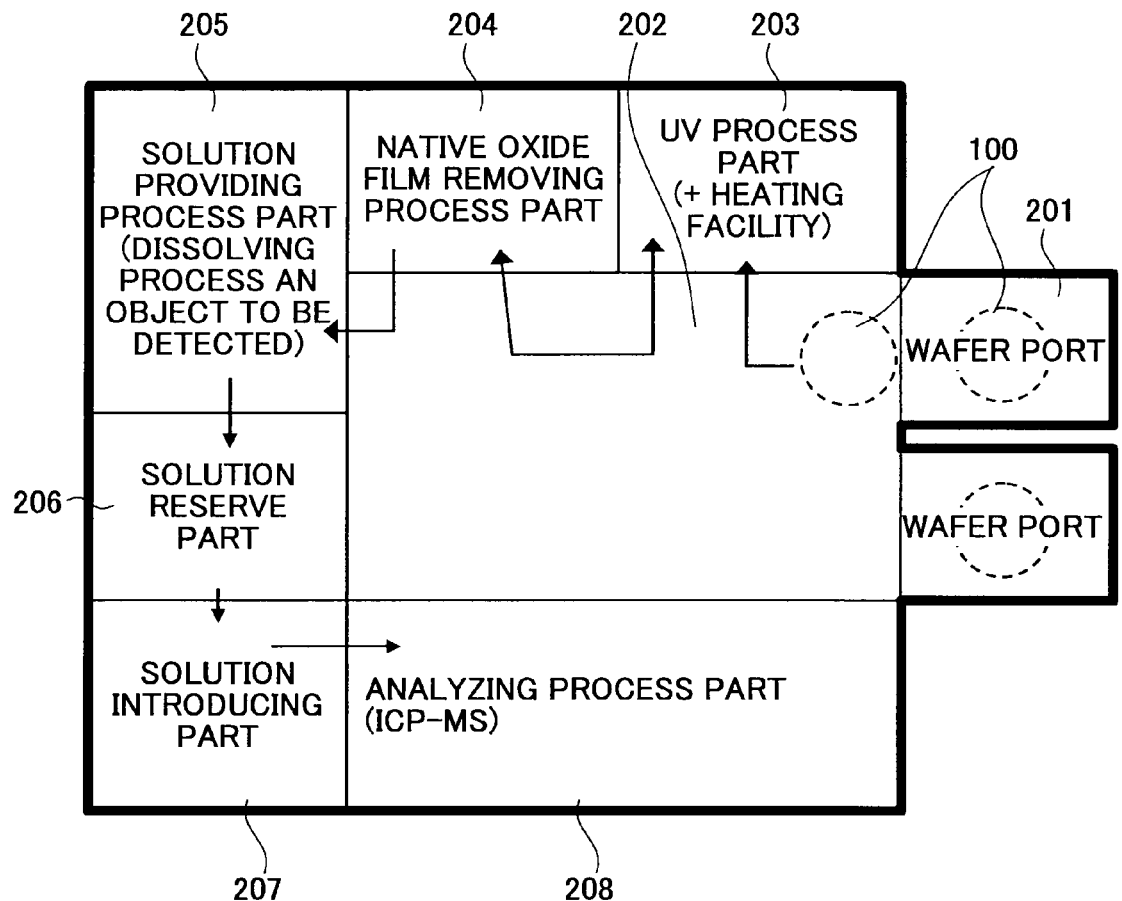

ANALYSIS METHOD AND ANALYSIS APPARATUS

TECHNICAL FIELD

The present invention generally relates to an analysis method and an analysis apparatus for analyzing an object to be analyzed on a substrate.

BACKGROUND ART

As the performance of semiconductor apparatuses is improved, it becomes increasingly important to control contaminations during a fabrication process of such semiconductor apparatuses. For example, when a silicon (Si) substrate related to a semiconductor fabrication is contaminated, sometimes it happens that devices formed in the silicon substrate do not have sufficient characteristics for a required performance, and a yield of the semiconductor apparatus manufactured becomes lower. For example, as to detecting contaminations on a silicon (Si) substrate, there is a known method in which a solvent, such as hydrogen fluoride (HF) is dripped down onto the Si substrate for dissolving metal contaminants, and the solution is analyzed by an inductively coupled plasma mass spectroscopy (ICP-MS) method.

FIG. 1A-FIG. 1D are illustrative drawings showing an analysis method for analyzing metal contamination on a Si substrate 1. A process step is shown in FIG. 1B, for example, where a solution including HF is dripped down onto a Si substrate 1. Next, in the process steps shown in FIG. 1C-FIG. 1D, a spherical droplet 2 of the solution obtained by dripping is rolled over on the substrate 1, and it dissolves metals on the substrate.

In the next step, the solution 2 containing contaminant substances such as metal and the like, is collected. The solution 2 may then be analyzed using for example the ICP-MS method, so that metallic contaminations on the Si substrate can be qualitatively or quantitatively analyzed.

Patent Reference 1 Japanese Patent Application Publication No. 8-237709.

However, when a film is formed on an object to be analyzed on a silicon (Si) substrate, there is difficulty to apply the above analysis method.

FIG. 2A is an illustrative drawing showing a Si substrate 1 to be analyzed and a film 3 formed on the Si substrate 1. When the film 3 is formed on the Si substrate 1, it becomes difficult to dissolve metal on the Si substrate 1 by using a solution.

For example, in a plasma etching process using fluorocarbon related gas ($CF_4$, $CHF_3$, and the like), a film of fluorocarbon related substances may form on a substrate. Such fluorocarbon related film has a property of low solubility against a HF (hydrofluoric acid) related solution (or a vapor of HF). Therefore, it is difficult to analyze contamination of a substrate processed with plasma etching equipment.

Further, as a surface of a fluorocarbon related film including oxygen atoms has lower wettability (larger hydrophilicity) than that of a Si surface, as shown in FIG. 2B, when a droplet of a solution 2 is dropped onto the film surface, the solution spreads over the film surface, so that it becomes difficult to roll over the droplet on the film surface.

In addition, for removing the film, when a plasma etching process or a sputtering process is performed on the substrate, contaminant materials can disperse. Moreover another contaminant material can be generated, making it difficult to maintain the accuracy of the analysis.

SUMMARY OF THE INVENTION

The present invention provides a novel and useful analysis method that solves problems and an analysis apparatus that is capable of performing the analysis method.

According to one aspect of the present invention, there is provided an analysis method that is capable of analyzing an object to be analyzed on a substrate covered with a film, and to provide an analysis apparatus that is capable of performing the analysis method.

In one embodiment of the present invention, there is provided an analysis method including a first step of removing a film formed on a substrate due to irradiating ultraviolet light, a second step of providing a solution onto a surface of the substrate for dissolving an object being analyzed on the substrate, and a third step of analyzing the object being analyzed in the solution that is used in the second step.

According to an aspect of the present invention, when an object to be analyzed on a substrate is covered with a film, an analysis method and an analysis apparatus, which enables analyzing the object to be analyzed existing on the substrate with excellent accuracy, are provided.

BRIEF DESCRIPTION OF THE DRAWINGS

FIG. 10 is an illustrative drawing showing an analysis apparatus according to a second embodiment.

DISCLOSURE OF THE INVENTION

First Embodiment

An analysis method according to a first embodiment of the present invention includes 1) a first step of removing a film formed on a substrate by irradiating ultraviolet light, 2) a second step of providing a solution on the substrate to dissolve the object to be analyzed on the substrate, 3) a third step of analyzing the object to be analyzed in the solution used in the second step.

For analyzing metal or the like, when an object to be analyzed on a substrate is covered by a film of a fluorocarbon related substance (a film including an element C or an element F, and having a material such as a C—C bond, a C—F bond), there is difficulty in dissolving the object to be analyzed by a solution.

Removing a film by ultraviolet light radiation, unlike an etching method or sputtering method which raise a concern about dispersing the object to be analyzed, has a gentle reaction, so that there is less concern about generating additional contamination. Thereby, it becomes possible to analyze the object to be analyzed with high accuracy.

Irradiating ultraviolet light causes the materials consisting of fluorocarbon related film to dissociate (breaking its bonds). Further, it is preferable that oxygen is included in the atmosphere, as activated oxygen enhances an etching effect.

An analysis method will now be explained with reference to the figures.

Figure 1A:
FIG. 1A is an illustrative drawing showing a step of a conventional analysis method.
Figure 1B:
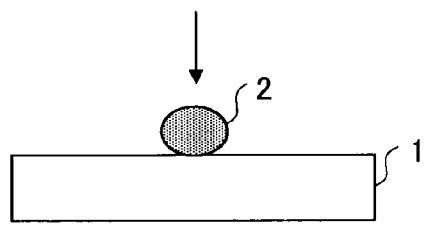
FIG. 1B is an illustrative drawing showing another step of a conventional analysis method.
Figure 1C:
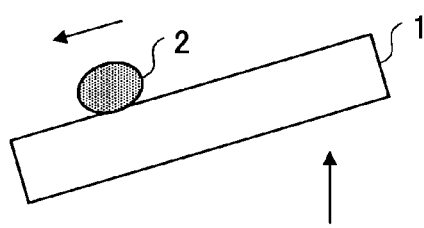
FIG. 1C is an illustrative drawing showing another step of a conventional analysis method.
Figure 1D:
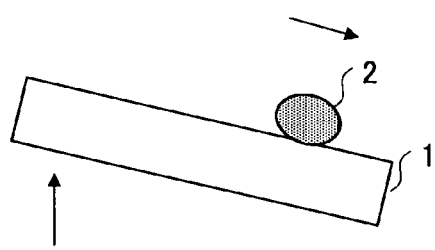
FIG. 1D is an illustrative drawing showing another step of a conventional analysis method.
Figure 2A:
FIG. 2A is an illustrative drawing showing a problem of a conventional analysis method.
Figure 2B:
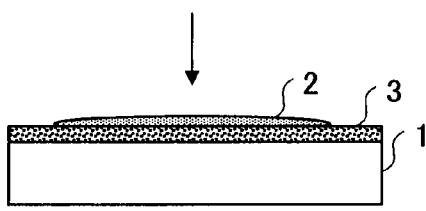
FIG. 2B an illustrative drawing showing another problem of a conventional analysis method.
Figure 3:
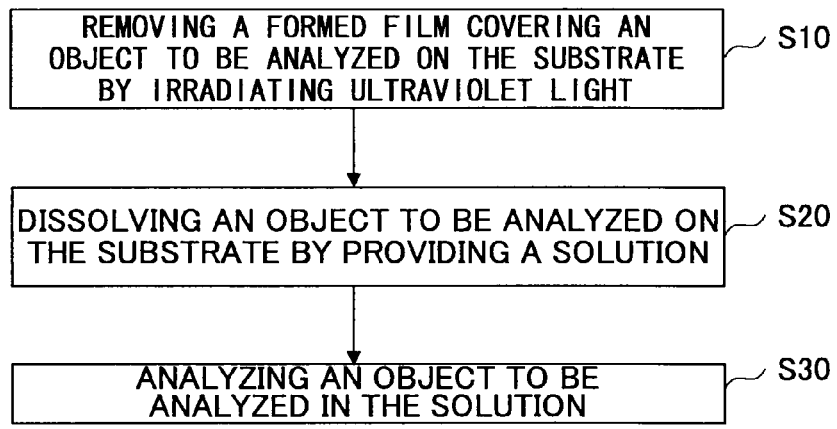
FIG. 3 is an illustrative drawing showing a flowchart of an analysis method according to a first embodiment.

FIG. 3 is a flowchart according to a first embodiment of the present invention, and FIG. 4A-FIG. 4D are illustrative drawings to show the process steps of the analysis method of the first embodiment of the present invention.

Figure 4A:
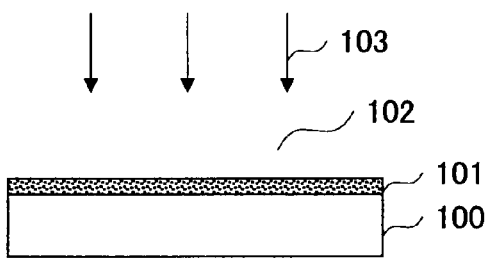
FIG. 4A is an illustrative drawing showing a step of an analysis method according to a first embodiment.

First, in step 10 in FIG. 3 (indicated as S10, the same manner in the following) a formed film covering an object to be analyzed on a substrate is removed by irradiating ultraviolet light. A step 10 is schematically shown in FIG. 4A. Referring to FIG. 4A, for example, a film 101 made of fluorocarbon related material on a substrate made of Si is removed by irradiating the film 101 with ultraviolet light 103 having a wavelength ranging from 100 nm to 320 nm. In a preferred embodiment, oxygen is included in the atmosphere 102 surrounding the substrate 100 (film 101). In addition to the effect the ultraviolet light 103 has in dissociating the film 101 this produces an effect in which the oxygen activated by the ultraviolet light enhances the effect of etching the film.

Further, as the reaction for removing the film is enhanced, it is preferable if the substrate 100 is heated to raise its temperature while the ultraviolet light is irradiated onto it. The substrate temperature may be, for example, at room temperature through about 400° C.

Figure 4B:
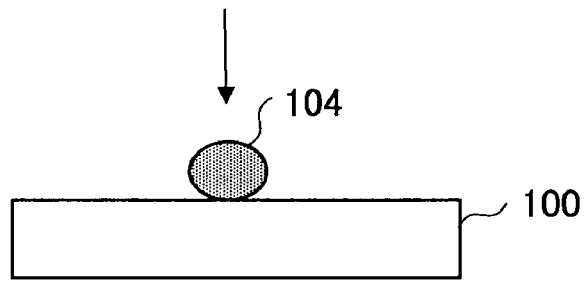
FIG. 4B is an illustrative drawing showing another step of the analysis method according to the first embodiment.
Figure 4C:
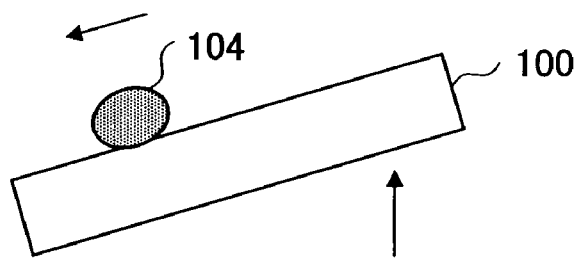
FIG. 4C is an illustrative drawing showing another step of the analysis method according to the first embodiment.
Figure 4D:
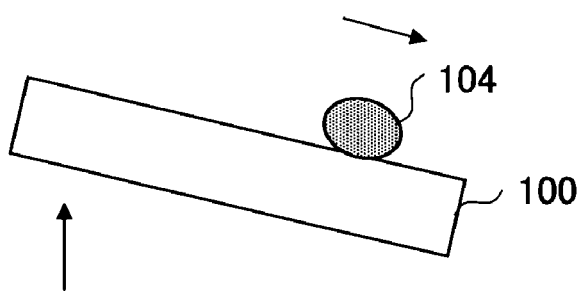
FIG. 4D is an illustrative drawing showing another step of the analysis method according to the first embodiment.

Next, in a step 20 of FIG. 3, a solution 104 is provided onto the substrate surface to dissolve the object to be analyzed sticking on the substrate surface. The step 20 is schematically shown in FIG. 4B-FIG. 4D. As shown in FIG. 4B, for the surface of the substrate 100 where the film 101 is removed, a solution 104 including for example a HF (hydrofluoric acid) is supplied (dripping). Further, as shown in FIG. 4C-FIG. 4D, by controlling the angle of declining the substrate 100, the solution 104 (droplet) is rolled over on it, and the object (e.g. metal or the like) to be analyzed on the substrate 100, sticking on the substrate, is dissolved with the solution 104.

Then, in a step 30 of FIG. 3 the solution 104 is collected and analyzed for example by the inductively coupled plasma mass spectroscopy (ICP-MS) method, and then the object (metal) to be analyzed is qualitatively or quantitatively analyzed. For analyzing the solution 104 above, the analysis method is not limited to ICP-MS, for example, the inductively coupled plasma atomic absorption spectrometry (ICP-AAS), the atomic absorption spectrometry (AAS), or a known method can be applied.

Thus, it becomes possible to analyze the object to be analyzed (contamination on the substrate 100) stuck on the substrate 100.

According to the present embodiment, even if a film is formed on a substrate, analyzing (detecting) the object to be analyzed on the substrate is possible with excellent accuracy.

For example, in plasma etching process equipment which uses fluorocarbon related gas ($CF_4$, $CHF_3$, the like), a fluorocarbon related film having resistance to HF solution for removal is formed on the substrate in some cases. Thus, once such a HF-resistant fluorocarbon related film is formed on a substrate, it becomes difficult to analyze an object to be analyzed on the substrate.

In the analysis method according to the present embodiment, a film is removed by ultraviolet light irradiation for making it easier to collect the object to be analyzed. The removal of a film by using irradiating ultraviolet light, unlike the aforementioned etching method or a sputtering method, has less concern about dispersing the object to be analyzed, and the reaction is gentle, so that there is less concern about generating additional contamination. Thereby, it becomes possible to analyze the object to be analyzed with high accuracy.

Further, as shown in FIG. 4A, while ultraviolet light 103 is irradiated onto the film 101, if oxygen is included in the atmosphere 102, the oxygen is activated by the ultraviolet light. When oxygen is included in the atmosphere 102 surrounding the film 101, in addition to the effect of the ultraviolet light that dissociates the film, the activated oxygen enhances an etching effect, so that the effect of removing the film is improved. For example, the process of a step 10 (FIG. 4A) may be performed in air containing oxygen, and if necessary, atmosphere including modified concentrations of oxygen, nitrogen, or the like may be used.

Figure 5:
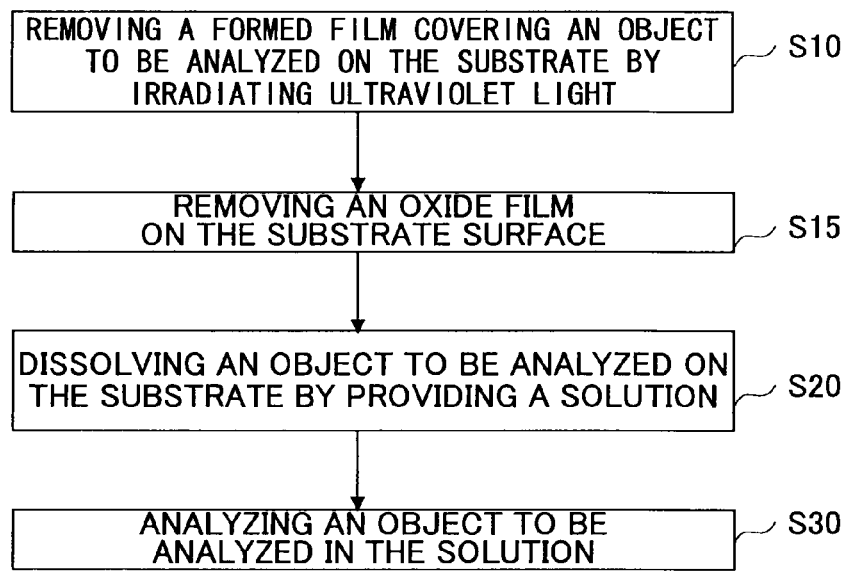
FIG. 5 is an illustrative drawing showing a variation of the FIG. 3 analysis method.

The analysis method shown in FIG. 3 may be modified as shown in FIG. 5. FIG. 5 is a variation of the analysis method shown in FIG. 3, where identical steps explained above are identified with the same reference characters and their explanations are omitted.

Referring to FIG. 5, a step 15 is provided between the step 10 and the step 20 that are described above. In step 15, an oxide film ($SiO_2$) consisting of Si formed on a Si substrate 100 is removed. The removal of the oxide film is performed, for example, by supplying a vapor of HF onto the substrate 100. The present step may be omitted, in which case removing the oxide film may be performed as dissolving an object to be analyzed substantially at the same time by using the solution 104 provided in the step 20.

When the step 15 is provided, the removal of oxide film using the solution 104 is not necessary, and the amount of the solution 104 provided to the substrate 100 in the step 20 can be reduced. Thereby, it is effective to improve the accuracy of the analysis of the object to be analyzed.

In the analysis method shown in FIG. 5, the substrate 101 may be heated and processed with HF treatment alternately to have the fluorocarbon related film contracted and expanded so that it becomes easier to remove the oxide film. For example, in the analysis method, after the step 10 of raising the substrate temperature to a range from room temperature to about 400° C., the substrate temperature is lowered to room temperature, and then performed with the process corresponding to the step 15 (HF process). Next, the substrate is heated again to about 300° C., further the substrate temperature is lowered to room temperature, and then the substrate is processed with a treatment corresponding to the step 15 (HF process). According to this process, the removal of the oxide film becomes easier due to expanding and contracting of the film.

Figure 6:
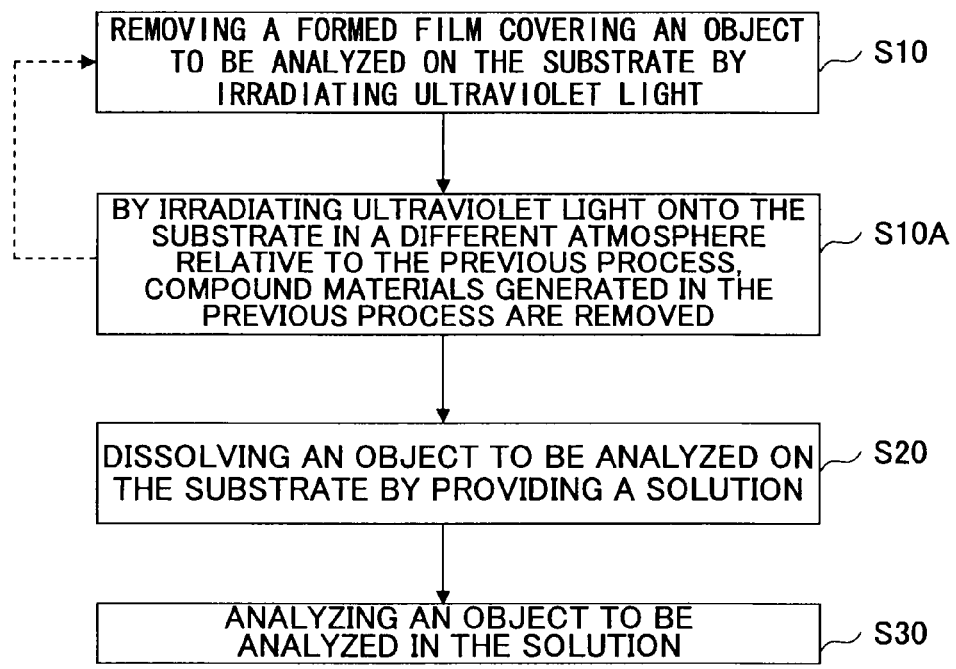
FIG. 6 is an illustrative drawing showing another variation of the FIG. 3 analysis method.

Further, the analysis method shown in FIG. 3 may be modified as shown in FIG. 6. FIG. 6 is a variation of the analysis method shown in FIG. 3. In the following, identical steps explained above are identified with the same reference numerals and their explanations are omitted.

Referring to FIG. 6, a step 10A is provided between the step 10 and the step 20. In the step 10A, due to irradiating ultraviolet light onto the substrate 100 in a different atmosphere from that of the step 10, it becomes possible to remove a compound material that is possibly generated in the step 10.

For example, in the step 10, for a certain condition of irradiating ultraviolet light or a particular composition of the film, an oxidizing reaction occurs and a resulting CO related compound may stick on the substrate 100.

In step 10A, by irradiating ultraviolet light onto the substrate 100 in hydrogen ($H_2$) atmosphere, the hydrogen is activated, and the activated hydrogen causes a reductive reaction that removes the compound materials (e.g. CO related compound) generated in the step 10. When necessary, step 10 and the step 10A may be performed alternately (that is, alternating of the oxidation and reductive reaction) to remove the film 101. Further, in the analysis method shown in FIG. 6, the step 15 (a step of removing an oxide film) shown in FIG. 5 may be performed following the step 10A.

Figure 7A:
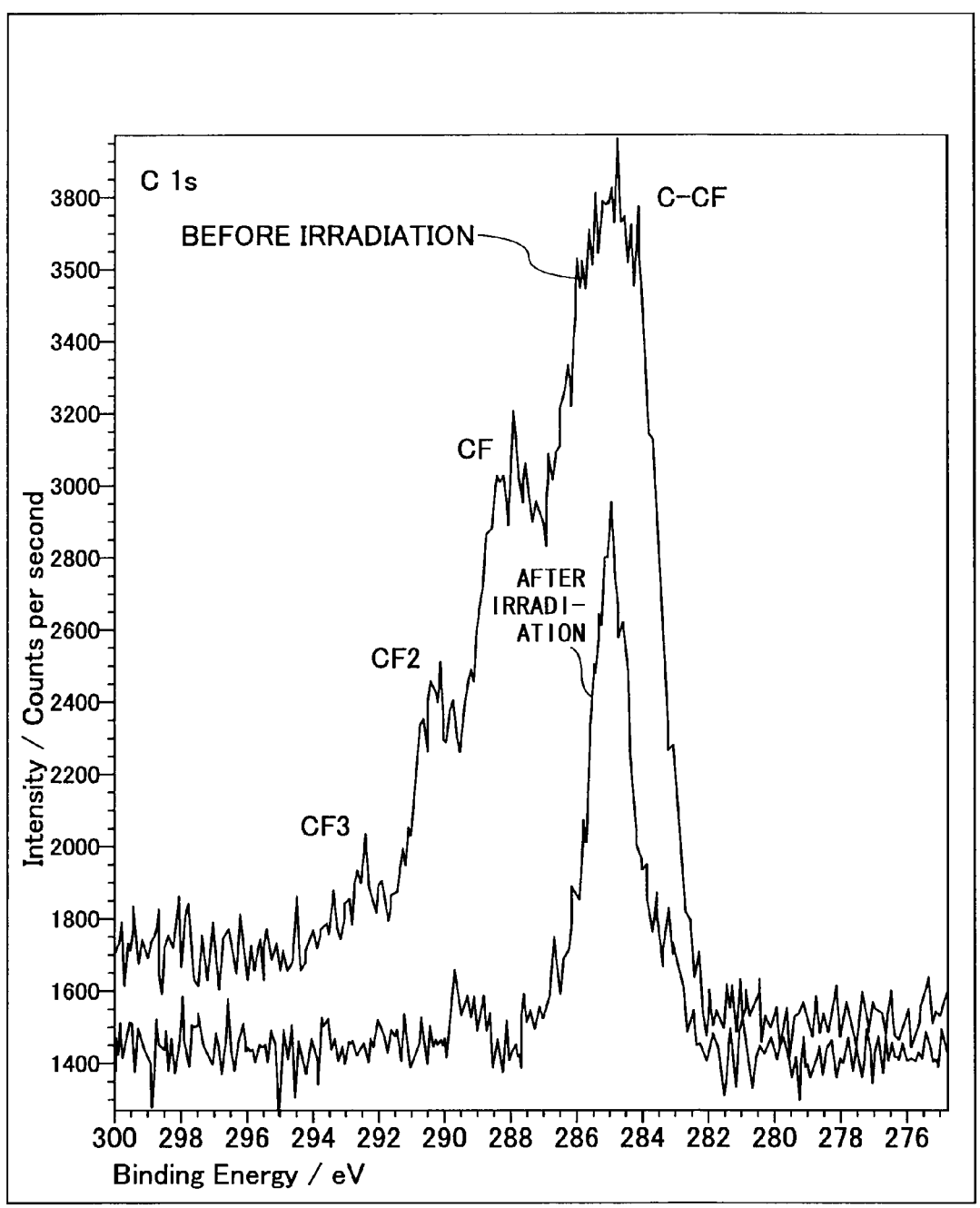
FIG. 7A is an illustrative drawing showing an example of an XPS analysis result of a substrate.
Figure 7B:
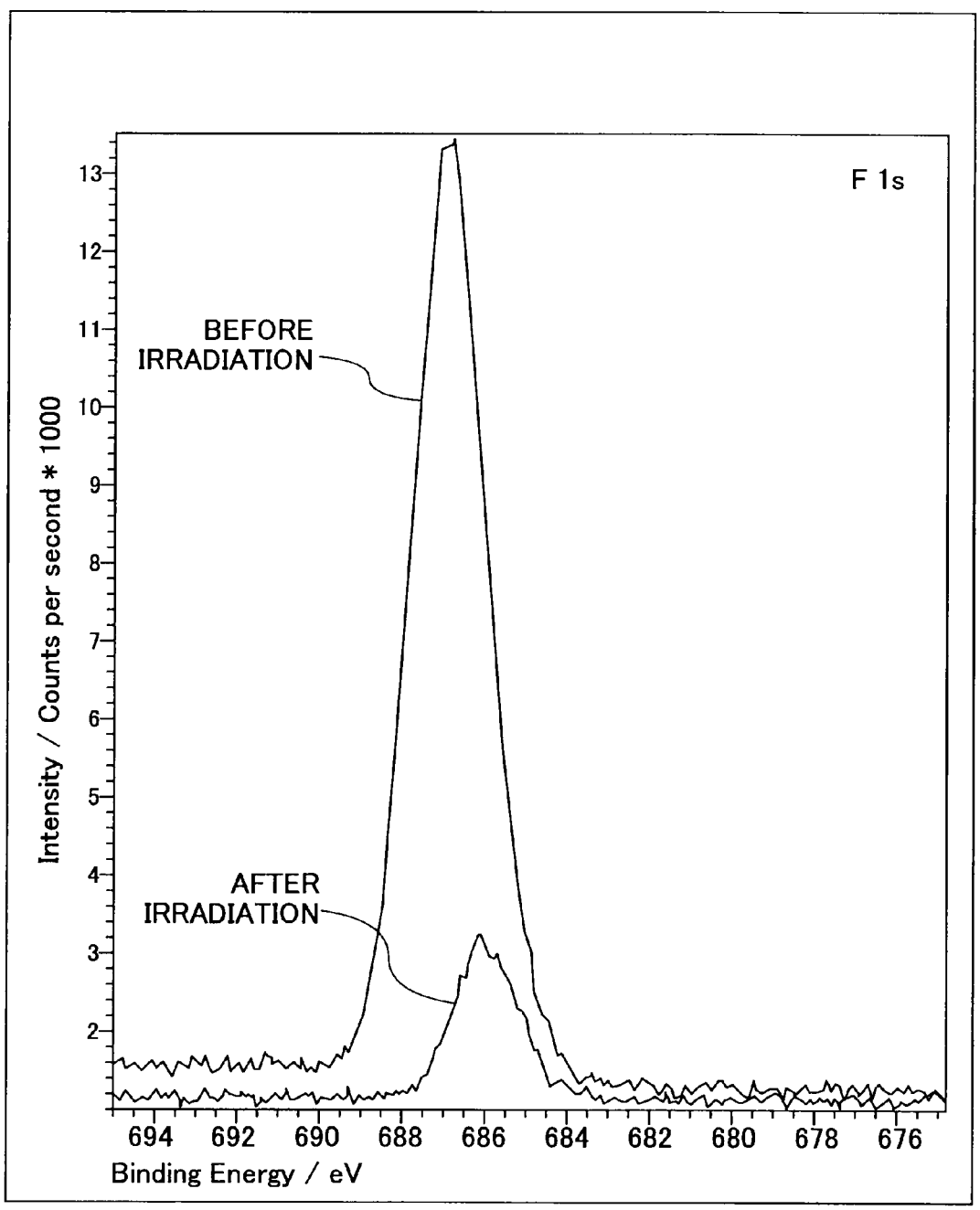
FIG. 7B is an illustrative drawing showing another example of an XPS analysis result of a substrate.

FIG. 7A and FIG. 7B are illustrative drawings showing, for a case in which a fluorocarbon related film is formed on a silicon substrate, the results of the spectra of X-ray Photoelectron Spectroscopy (XPS) measurement of the silicon surface for before and after ultraviolet light irradiation (before and after the step 10 of FIG. 3). FIG. 7A shows C1s spectra and FIG. 7B shows F1s spectra, respectively.

In the present measurement, the wavelength of the ultraviolet light is 172 nm, the substrate temperature is 200° C., and the ultraviolet light is irradiated for about 300 seconds onto the film with a thickness of about 6 nm.

Referring to FIG. 7A and FIG. 7B, the peaks of C—C bonds and C—F bonds relating to C and F in the film are lowered by the ultraviolet light irradiation, indicating that the fluorocarbon related film is removed.

Figure 8A:
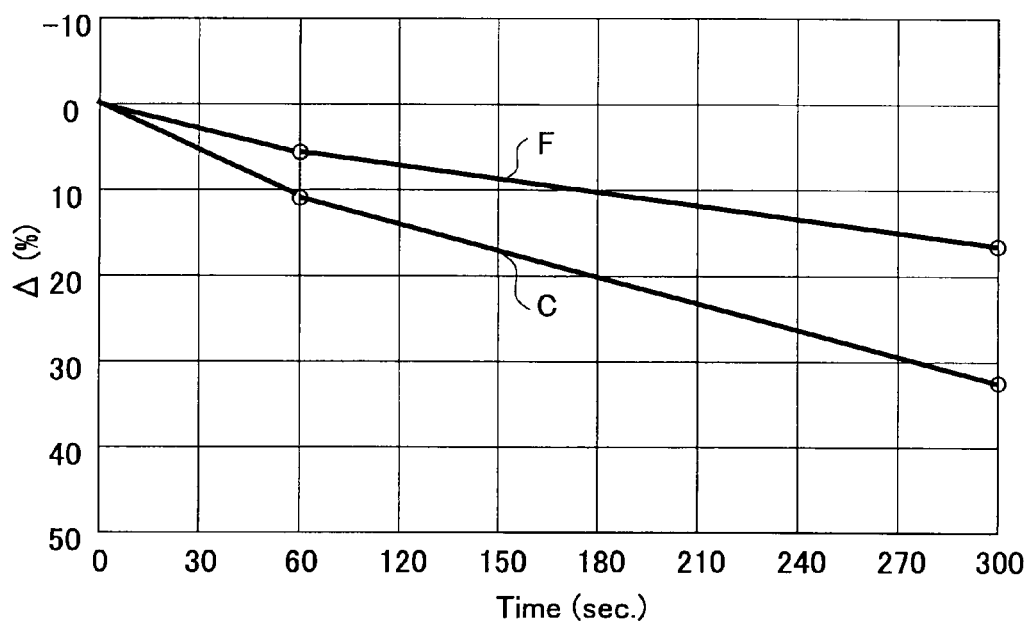
FIG. 8A is an illustrative drawing showing another example of an XPS analysis result of a substrate.
Figure 8B:
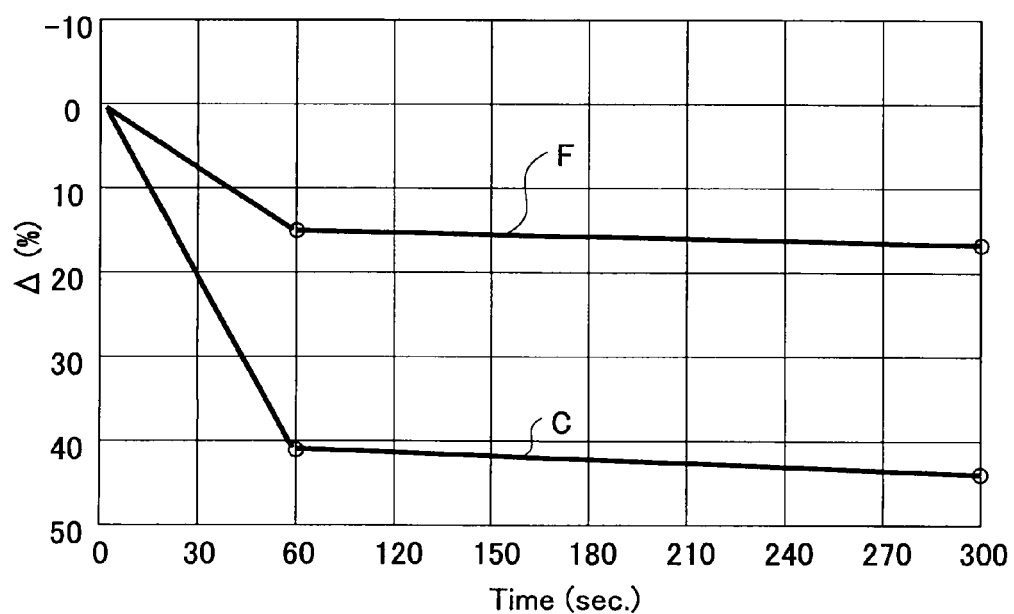
FIG. 8B is an illustrative drawing showing another example of an XPS analysis result of a substrate.

FIG. 8A and FIG. 8B indicate an element C (carbon) in the film and the reducing rates of element C as a function of time in the horizontal axis, calculated from the XPS spectra. The substrate temperatures are about room temperature in FIG. 8A and 200° C. for FIG. 8B, respectively.

It is seen in FIG. 8A that the elements C and F in the film are reduced by continuous irradiation of ultraviolet light. It is also seen in FIG. 8B that the removing rate of the film is enhanced by heating the substrate (e.g. about 200° C.), and then it is effective to remove the film.

Figure 9A:
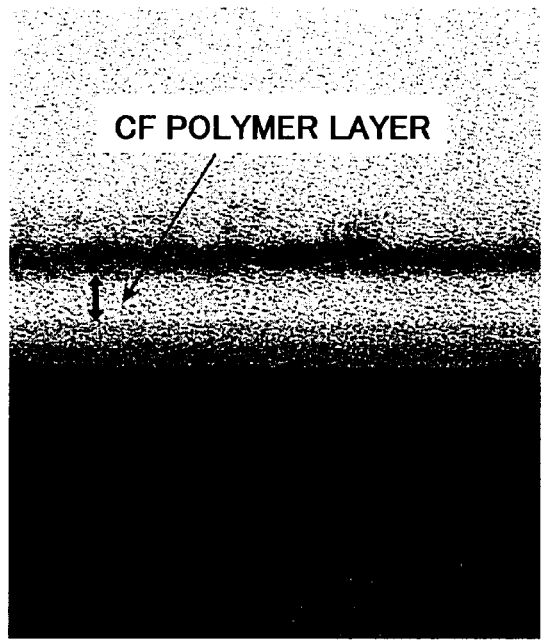
FIG. 9A is an illustrative drawing showing a cross sectional TEM photograph of a substrate before a film is removed.
Figure 9B:
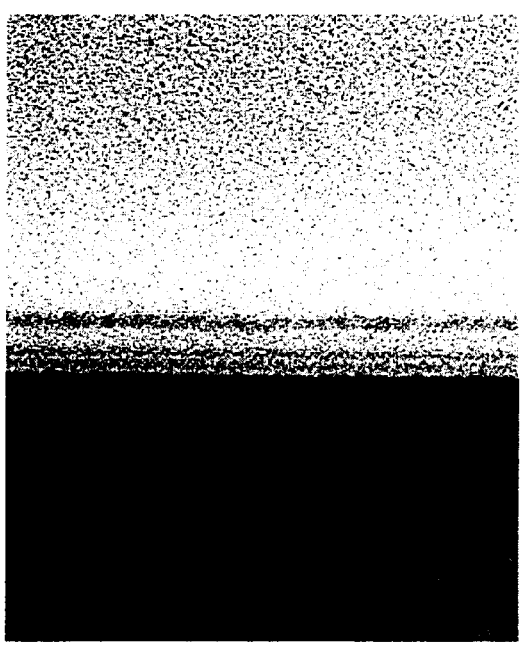
FIG. 9B is an illustrative drawing showing a cross sectional TEM photograph of a substrate after a film is removed.

Further, FIG. 9A is a transmission electron microscope (TEM) image showing a fluorocarbon related film (indicated as CF polymer layer) generated on a $SiO_2$ film on the Si substrate, and FIG. 9B is a TEM image of the film of FIG. 9A after being irradiated by ultraviolet light. In the present evaluation, the ultraviolet light used has a wavelength of 172 nm, the substrate temperature is about 200° C., the film thickness is about 6 nm, and the ultraviolet light is irradiated onto the substrate for 300 seconds.

Comparing FIG. 9A and FIG. 9B, it will be appreciated that a fluorocarbon related film has been removed.

Second Embodiment

FIG. 10 is an illustrative drawing showing a plan view of an analysis apparatus 200 for performing the analysis method described in the first embodiment.

Referring to FIG. 10, the analysis apparatus 200 includes a substrate transfer chamber 202, a wafer (substrate) port 201, UV process (irradiation) part 203, a native oxide film removing process part 204, a solution providing process part (a part of dissolving process of an object to be analyzed) 205, a solution reserve part 206, a solution introducing part 207, and an analyzing process part 208 surrounding to connect to the substrate transfer chamber 202. Further, the UV process part 203 may include a heating facility if necessary.

Further, as a material to construct the UV process part 203, generally, synthetic quartz is used. A single crystal sapphire or $BaF_2$ crystal (barium fluoride) may be used to prevent damages due to fluorine remaining on a substrate.

For the analysis apparatus, the process sequence to perform the analysis method according to the first embodiment is explained in the following.

First, by using transfer arms or the like (not shown), the substrate 100 is transferred from the wafer port 201 to the UV process part 203. In the UV process part 203, a process treatment, corresponding to the step 10 (FIG. 4A) of FIG. 3, is performed. Therefore, as shown in FIG. 4A, in terms of irradiating ultraviolet light 103 onto the film 101 formed on the substrate 100 in an atmosphere 102 including oxygen, the film 101 is removed. Further, if needed, the atmosphere 102 may be modified to that including hydrogen and ultraviolet light irradiation for removing a compound material generated in the step 10 (corresponding to the step 10A of FIG. 6). Further, the steps corresponding to the step 10 and the step 10A may be performed alternately in the UV process part 203.

Further, as described in the first embodiment, due to heating the substrate 100 after irradiating the ultraviolet light onto the substrate 100, it becomes easier to remove the film. Thus, the UV process part 203 may include a facility that is capable of heating the substrate 100.

Next, the substrate 100 is transferred to the native oxide film removing process part 204. Therefore, for the substrate 100, for example, by providing HF vapor onto the substrate 100, the film 101 formed on the substrate 100 is removed. Further, as explained above, the removal process of the oxide film in the native oxide film removing process part 204 may be omitted. Also, to make it more effective for removing the film 101 and oxide film, the substrate 101 may be transferred to the UV process part 203 again for additional ultraviolet irradiation and heating treatment.

The substrate 100 is then transferred to the solution providing process part 205. In the solution providing process part 205, a process treatment corresponding to the step 20 of FIG. 3 (FIG. 4B-FIG. 4D) is performed.

In the present case, as shown in FIG. 4B, for the surface of the substrate 100 on which the film 101 has been removed, a solution 104 including for example HF (hydrofluoric acid) is provided (dripped). Further, as shown in FIG. 4C-FIG. 4D, the declining angle is controlled so that the solution 104 (droplet) is rolled over on the substrate 100, and an object to be analyzed (e.g. metal or the like) sticking on the substrate 100 is sufficiently dissolved into the solution 104.

Next, the solution 104 including the dissolved object to be analyzed is collected into and reserved in the solution reserve part 206. Further, the solution 104 is introduced into the analysis process part 208 through the solution introducing part 207, and then it is analyzed by for example ICP-MS measurement equipment, and the object to be analyzed (metal) is analyzed qualitatively or quantitatively. The equipment used as the analysis process part 208 is not limited to ICP-MS, and the analysis process part 208 may include for example ICP-AAS equipment, or any analysis equipment that consists of AAS equipment.

Thereby, it becomes possible to analyze the object to be analyzed (contaminant on the substrate 100) sticking on the substrate 100.

According to the analysis equipment 200, the effect described in the first embodiment can be obtained. Further, in the analysis equipment 200, the substrate 100 and the solution 104 can be transferred immediately and processed continuously, so that it becomes possible to analyze the object to be analyzed with excellent accuracy.

As described above, the present invention is explained for preferable embodiments, the present invention is not limited to such particular embodiments above, and another variation or modification is possible in the scope described in the claims.

The present invention is based on the Japanese priority application 2006-196946 filed on Jul. 19, 2006, the entire contents of which are hereby incorporated herein by reference.

According to an aspect of the present invention, there is provided that an analysis method, and an analysis apparatus that, in a case in which an object to be analyzed is covered with a film, enable analyzing the object to be analyzed with excellent accuracy.

The invention claimed is:

1. A method for analyzing an object on a substrate comprising:
   a first step of removing a film formed on the substrate by irradiating the film with ultraviolet light,
   a second step of providing a solution onto a surface of the substrate from which the film is removed, for dissolving an object being analyzed sticking on the substrate, and
   a third step of analyzing the object being analyzed in the solution that is used in the second step.

2. The analysis method according to claim 1, wherein the film comprises a fluorocarbon related film.

3. The analysis method according to claim 2, wherein the first step is performed in a atmosphere including oxygen.

4. The analysis method according to claim 3, further comprising:
   another step of removing a compound material generated in the first step due to irradiating ultraviolet light in an atmosphere including hydrogen.

5. The analysis method according to claim 4, wherein the first step and the another step are performed alternately.

6. The analysis method according to claim 1, wherein the object being analyzed includes metal.

7. The analysis method according to claim 1, wherein the third step is performed by using a method of either an inductively coupled plasma mass spectroscopy, an inductively coupled plasma atomic absorption spectrometry, or an atomic absorption spectrometry.

8. The analysis method according to claim 1, wherein the substrate is a silicon substrate.

9. The analysis method according to claim 8, further comprising:
   another step of removing oxide film formed on the silicon substrate.

10. The analysis method according to claim 1, further comprising:
    a heating step for heating the substrate after the ultraviolet light irradiation.

11. An analysis apparatus, comprising:
    a first process part for removing a film formed on a substrate by irradiating the film with ultraviolet light,
    a second process part for providing a solution onto a surface of the substrate from which the film is removed, for dissolving an object being analyzed sticking on the substrate, and
    a third process part for analyzing the object being analyzed in the solution that is used in the second part.

12. The analysis apparatus according to claim 11, further comprising:
    a heating facility for heating the substrate after being irradiated with ultraviolet light.

* * * * *